(12) United States Patent
Rüegg et al.

(10) Patent No.: US 6,403,531 B1
(45) Date of Patent: Jun. 11, 2002

(54) HERBICIDAL SYNERGISTIC COMPOSITION AND METHOD OF WEED CONTROL

(75) Inventors: Willy Rüegg, Gipf-Oberfrick; Manfred Hudetz, Rheinfelden, both of (CH)

(73) Assignee: Syngenta Crop Protection, inc., Greensboro, NC (US)

( * ) Notice: Subject to any disclaimer, the term of this patent is extended or adjusted under 35 U.S.C. 154(b) by 0 days.

(21) Appl. No.: 09/664,111

(22) Filed: Sep. 18, 2000

Related U.S. Application Data

(62) Division of application No. 09/013,012, filed on Jan. 26, 1998, now Pat. No. 6,180,563.

(30) Foreign Application Priority Data

Jan. 28, 1997 (CH) .................................................. 178/97

(51) Int. Cl.⁷ ........................ A01N 43/54; A01N 43/70; A01N 33/10; A01N 47/30
(52) U.S. Cl. ...................................... 504/134; 504/136
(58) Field of Search ................................ 504/128, 136, 504/134

(56) References Cited

U.S. PATENT DOCUMENTS

| 4,579,583 A | 4/1986 | Fory et al. ...................... 71/92 |
| 5,002,606 A | 3/1991 | Moser et al. ................... 71/118 |
| 5,183,492 A | 2/1993 | Suchy et al. ................. 504/243 |

FOREIGN PATENT DOCUMENTS

| EP | 0 103 543 | 3/1984 | |
| JP | 02-160706 | 6/1990 | |
| WO | WO92/16522 | 10/1992 | .......... A01N/47/36 |
| WO | WO 96/32013 | 10/1996 | |
| WO | WO 97/34484 | 9/1997 | |
| WO | WO 97/41112 | 11/1997 | |

OTHER PUBLICATIONS

The Pesticide Manual, 10ᵗʰ ed. British Crop Protection Council, 1994, p. 549–550, 49–50, 32–33, 51–52, 565–566, 840–841, 740–741, 239–241, 956–957, 699–700, 959–960, 962–963, 974–975, 375–376, 271–274, 888–889, 542–545, 541–542, 898–899, 441–442, 623, 471–472, 848–849, 298–300, 376–378, 490–491, 947–948, 975–976, 1025–1026, 779–780, 121–123, 835–836, 693–694, 10–11, 21–22, 220–221, 909–910, 214–215, 577–578, 767–769, 683–685.

J. March, Advanced Org. Chem., John Wiley and Sons, 4ᵗʰ Edition, 1992,: Phase Transfer Catalysis, p. 362.
Agrow, No. 261, Aug. 2, 1996, p. 23.
Agrow, No. 247, Jan. 5, 1996, p. 19.

*Primary Examiner*—S. Mark Clardy
(74) *Attorney, Agent, or Firm*—William Teoli, Jr.; Thomas Hamilton

(57) ABSTRACT

A herbicidal composition comprising, in addition to conventional inert formulation adjuvants, the compound of formula I

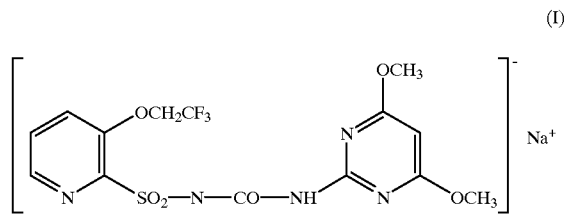

in admixture with a second component comprising at least one compound selected from the group consisting of ametryn, atrazine, hexazinone, asulam, diuron, 2,4-D, halosulfuron and butafenacil-allyl.

5 Claims, No Drawings

HERBICIDAL SYNERGISTIC COMPOSITION AND METHOD OF WEED CONTROL

This application is a divisional of Ser. No. 09/013,012, filed Jan. 26, 1998, now U.S. Pat. No. 6,180,563.

The present invention relates to a novel herbicidal synergistic composition comprising a combination of herbicidal active ingredients, which composition is suitable for selective weed control in crops of useful plants, for example in crops of cereals, cotton, soybeans, sugar beet, sugar cane, plantations crops, rape, maize and rice. The invention further relates to a method of controlling weeds in crops of useful plants and to the use of the novel composition for that purpose.

The compound of formula I

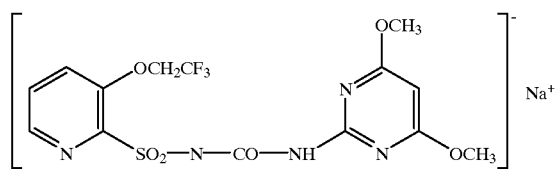

(I)

has herbicidal activity.

The following compounds are also known as herbicides and some of them are also available commercially:

compounds of formula II

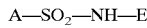

(II), wherein A is the group $A_1$

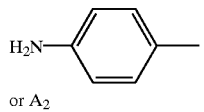

(A₁)

or $A_2$

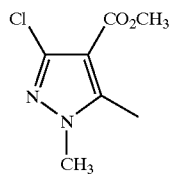

(A₂)

and E is the group $E_1$ COOCH₃ ($E_1$) or $E_2$

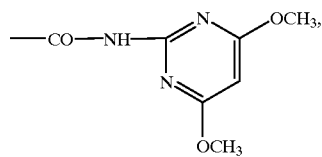

(E₂)

are known, for example, from The Pesticide Manual, 10th ed. British Crop Protection Council 1994, pages 549 and 49; compounds of formula III

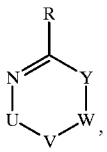

(III)

wherein U—V is a group of the formula $R_1C$=N, N=$CR_1$, $CONR_1$, $R_1NCO$ or $R_1C$=$CR_2$, wherein $R_1$ is —NHC₃H₇-(iso), —NHC(CH₃)₂CN, —NHC₄H₉-(tert), —NHC₂H₅,

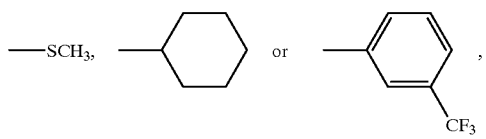

W—Y is a group of the formula $CR_2$=N, $CONR_2$, $NR_2CO$, $CONR_3$ or $CR_2$=$CR_3$, wherein $R_2$ is methyl, —Cl, —NH₂, —NHC₃H₇-(iso) or —NHC₂H₅ and $R_3$ is —NHCH₃ or C₄H₉-(tert), and R is —Cl, —SCH₃, —C₄H₉-(tert), methoxy, hydroxy, N(CH₃)₂, CHF₂ or hydrogen; or U—V—W—Y together form the group —C(CF₃)=C(R₄)—C(CH₂—C₃H₇-(iso))=C(R₅)—, wherein $R_4$ is —COSCH₃ or

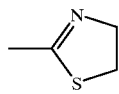

and $R_5$ is COOCH₃ or COSCH₃, are known, for example, from The Pesticide Manual, 10th ed. British Crop Protection Council 1994, pages 32, 51, 565, 840, 740, 239, 956, 699, 959, 962, 974 and 375; compounds of formula IV

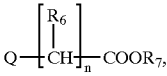

(IV)

wherein n is 0 or 1, $R_6$ is hydrogen, —CH₃ or —NH₂, $R_7$ is hydroxy, C₂H₅, Na⁺, —CH(CH₃)₂—CO₂—CH=CH₂, —C₄H₉-n or —CH₂—CH₂—O—N=C(CH₃)₂, and Q is the group

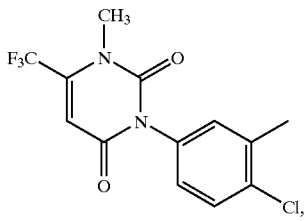

(Q₁)

-continued (Q₂) 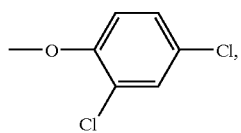

(Q₃) 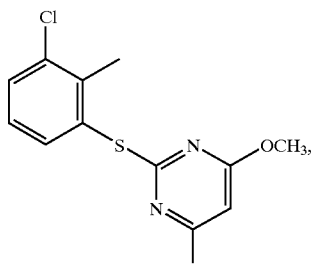

(Q₄) 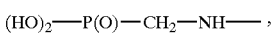

(Q₅) 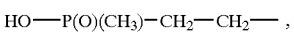

(Q₆) 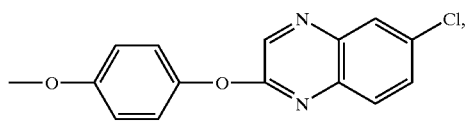

(Q₇) 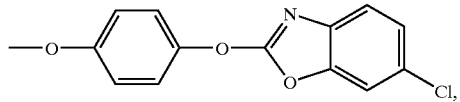

(Q₈) 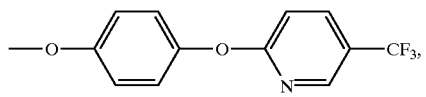

(Q₉) 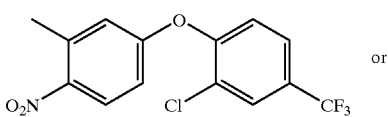

or (Q₁₀) 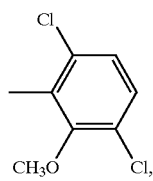

are known, for example, from The Pesticide Manual, 10th ed. British Crop Protection Council 1994, pages 271, 888, 542, 541, 898, 441, 623, 471, 848 and 298, and from U.S. Pat. No. 5,183,492;

compounds of formula V (V) 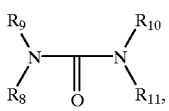

wherein $R_8$ is the group

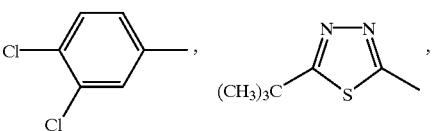

3-trifluoromethylphenyl or phenyl, $R_9$ and $R_{10}$ are each independently of the other hydrogen or methyl and $R_{11}$ is methyl or the group

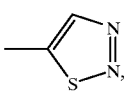

are known, for example, from The Pesticide Manual, 10th ed. British Crop Protection Council 1994, pages 376, 490, 947 and 975;

compounds of formula VI (VI) 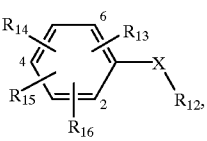

wherein X is —NH— or —NC₃H₇-(n), $R_{12}$ is —C₃H₇-(n) or CH(C₂H₅)₂, or X and $R_{12}$ together are cyano, $R_{13}$ is 2-NO₂ or 3-Br, $R_{14}$ 4-CF₃, 4-CH₃ or 4-OH, $R_{15}$ 6-NO₂ or 5-Br, and $R_{16}$ is 3-CH₃ or 5-NH₂, are known, for example, from The Pesticide Manual, 10th ed. British Crop Protection Council 1994, pages 1025, 779, 121 and 835;

compounds of formula VII $$Z—N(R_{17})—R_{18} \qquad (VII),$$

wherein

Z is the group

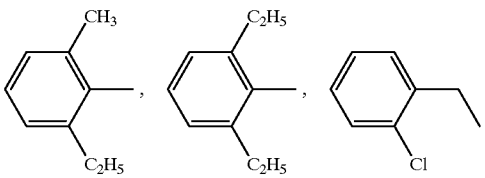

or

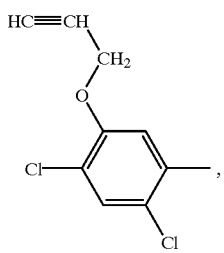

$R_{17}$ is —CH(CH$_3$)—CH$_2$OCH$_3$,

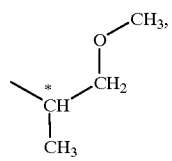

CH$_2$OC$_2$H$_5$ or —CH$_2$OCH$_3$, $R_{18}$ is —C(O)—CH$_2$Cl or $R_{17}$ and $R_{18}$ together are the group —C(O)—C(CH$_3$)$_2$—CH$_2$—O— or

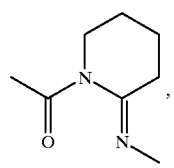

are known, for example, from The Pesticide Manual, 10th ed. British Crop Protection Council 1994, pages 693, 10, 21 and 220, and from AGROW No. 247, 5.1. (1996) page 19 and U.S. Pat. No. 5,002,606;

compounds of formula VIII

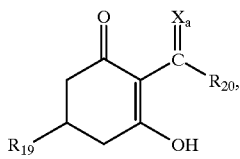

(VIII)

wherein $R_{19}$ is hydrogen or —CH$_2$—CH(CH$_3$)—SC$_2$H$_5$, $R_{20}$ is —C$_2$H$_5$, —C$_3$H$_7$-(n) or

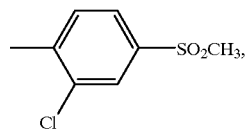

and $X_a$ is oxygen, NOC$_2$H$_5$ or NOCH$_2$—CH=CHCl (trans), are known, for example, from The Pesticide Manual, 10th ed. British Crop Protection Council 1994, pages 909, 214 and 577;

compounds of formula IX

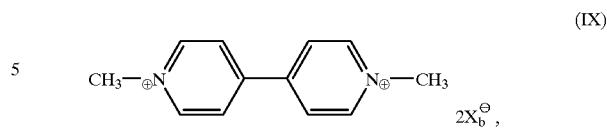

(IX)

wherein $X_b$ is chlorine or CH$_3$SO$_3$, are known, for example, from The Pesticide Manual, 10th ed. British Crop Protection Council 1994, page 767;

the compound of formula X

CH$_3$—As(O)—(OH)$_2$ (X), and its salts, especially the monosodium and disodium salts, are known, for example, from The Pesticide Manual, 10th ed. British Crop Protection Council 1994, page 683.

Surprisingly, it has now been found that a combination of two active ingredients in variable proportions, i.e. a combination of the active ingredient of formula I with one of the above-mentioned active ingredients of formulae II to X, has a synergistic effect that is capable of controlling, both pre-emergence and post-emergence, the majority of weeds occurring especially in crops of useful plants without significantly damaging the useful plants. According to the present invention, therefore, a novel synergistic composition for selective weed control is proposed that comprises as active ingredient, in addition to conventional inert formulation adjuvants, the compound of formula I

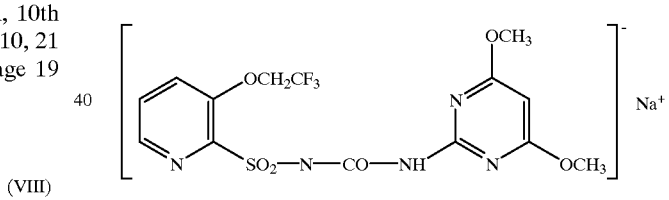

(I)

in admixture with a synergistically effective amount of at least one compound from the substance classes of formula II

A—SO$_2$—NH—E (II), wherein A is the group $A_1$

(A$_1$)

or A$_2$

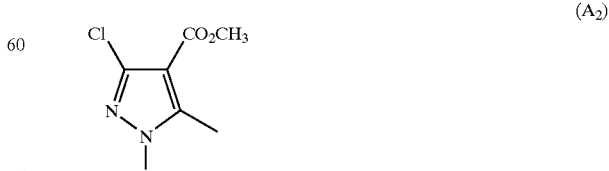

(A$_2$)

and E is the group E₁ COOCH₃ (E₁) or E₂

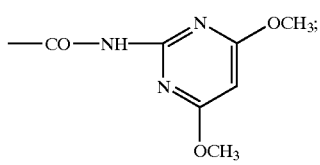 (E₂)

of the formula III

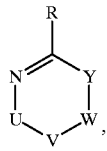 (III)

wherein U—V is a group of the formula R₁C=N, N=CR₁, CONR₁, R₁NCO or R₁C=CR₂, wherein R₁ is —NHC₃H₇-(iso), —NHC(CH₃)₂CH, —NHC₄H₉-(tert), —NHC₂H₅, —SCH₃,

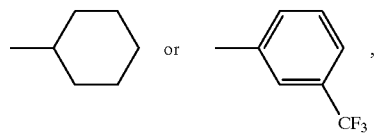

W—Y is a group of the formula CR₂=N, CONR₂, NR₂CO, CONR₃ or CR₂=CR₃, wherein

R₂ is methyl, —Cl, —NH₂, —NHC₃H₇-(iso) or —NHC₂H₅ and

R₃ is —NHCH₃ or C₄H₉-(tert), and

R is —Cl, —SCH₃, —C₄H₉-(tert), methoxy, hydroxy, N(CH₃)₂, CHF₂ or hydrogen; or

U—V—W—Y together form the group —C(CF₃)=C(R₄)—C(CH₂—C₃H₇-(iso))=C(R₅)—, wherein R₄ is —COSCH₃ or

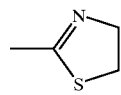

and

R₅ is COOCH₃ or COSCH₃;

of formula IV

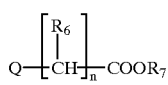 (IV)

wherein n is 0 or 1, R₆ is hydrogen, —CH₃ or —NH₂,

R₇ is hydroxy, C₂H₅, Na⁺, —CH(CH₃)₂—CO₂—CH=CH₂, —C₄H₉-n or —CH₂—CH₂—O—N=C(CH₃)₂, and Q is the group

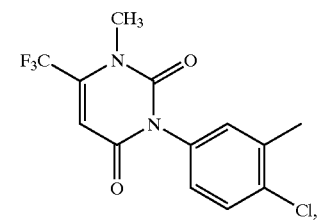 (Q₁)

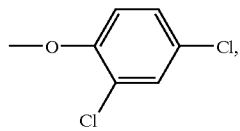 (Q₂)

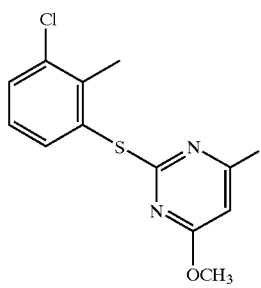 (Q₃)

 (Q₄)

(HO)₂—P(O)—CH₂—NH—,

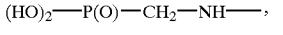 (Q₅)

HO—P(O)(CH₃)—CH₂—CH₂—,

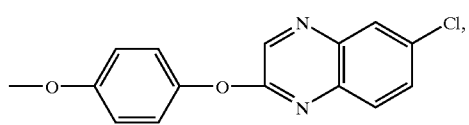 (Q₆)

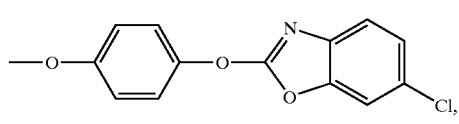 (Q₇)

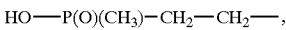 (Q₈)

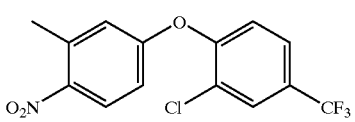 (Q₉)

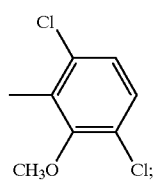 (Q₁₀)

of formula V (V)

wherein $R_8$ is the group 3-trifluoromethylphenyl or phenyl, $R_9$ and $R_{10}$ are each independently of the other hydrogen or methyl and $R_{11}$ is methyl or the group of formula VI (VI)

wherein

X is —NH— or —NC$_3$H$_7$-(n), $R_{12}$ is —C$_3$H$_7$-(n) or CH(C$_2$H$_5$)$_2$, or X and $R_{12}$ together are cyano, $R_{13}$ is 2-NO$_2$ or 3-Br, $R_{14}$ 4-CF$_3$, 4-CH$_3$ or 4-OH, $R_{15}$ 6-NO$_2$ or 5-Br, and $R_{16}$ is 3-CH$_3$ or 5-NH$_2$;

of formula VII $$Z-N(R_{17})-R_{18} \quad (VII),$$

wherein

Z is the group $R_{17}$ is —CH(CH$_3$)—CH$_2$OCH$_3$,

—CH$_2$OC$_2$H$_5$ or —CH$_2$OCH$_3$, $R_{18}$ is —C(O)—CH$_2$Cl or $R_{17}$ and $R_{18}$ together are the group —C(O)—C(CH$_3$)$_2$—CH$_2$—O— or of formula VIII (VIII)

wherein $R_{19}$ is hydrogen or —CH$_2$—CH(CH$_3$)—SC$_2$H$_5$, $R_{20}$ is —C$_2$H$_5$, —C$_3$H$_7$-(n) or and $X_a$ is oxygen, NOC$_2$H$_5$ or NOCH$_2$—CH=CHCl (trans);

of formula IX (IX)

wherein $X_b$ is chlorine or CH$_3$SO$_3$;

and of formula X $$CH_3-As(O)-(OH)_2 \quad (X),$$

and salts thereof.

The sulfonylurea compound of formula $F_1$ ($F_1$)

which corresponds to the salt of formula I Is known, for example, from EP-A-0 103 453. By reaction with suitable salt-forming agents the compound of formula $F_1$ can be converted into the compound of formula I in a conventional manner known per se. Such salt-forming agents are, in principle, all bases that are capable of abstracting the acid hydrogen atom in the $SO_2$—NH—CO— grouping. There have been found to be especially advantageous in this connection hydrides, hydroxides, alcoholates, hydrogen carbonates and carbonates of sodium. The reaction of the compound of formula $F_1$ with the bases to form the compound of formula I is carried out in a manner known per se, preferably in protic or aprotic solvents at room temperature or elevated temperature, in which reaction crown ethers and/or phase transfer catalysts may be present as is described, for example, in J. March, Advanced Org. Chem., John Wiley and Sons, 4th Edition, 1992: Phase Transfer Catalysis, page 362. For example, the compound of formula I can be obtained in good yields by simply stirring the compound of formula $F_1$ with aqueous sodium hydroxide solution at room temperature. Such methods are described, for example, in WO 97/41112.

According to the invention, preference is given to compositions that comprise the compound of formula I and at least one compound selected from the compounds ametryn, atrazine, hexazinone, asulam, diuron, 2,4-D, halosulfuron and the compound of formula IV wherein Q is $Q_1$, $R_7$ is —$C(CH_3)_2$—$C(O)O$—$CH_2CH$=$CH_2$ and n is 0. Of those compositions, special, preference is given to those that comprise the compound of formula I and at least one compound selected from the compounds ametryn, atrazine, hexazinone and asulam. Prominence is to be given also to compositions that comprise the compound of formula I and at least one compound selected from the compounds fluometuron, prometryn, metolachlor, α-metolachlor, norflurazon, pyrithiobac-sodium, DSMA, MSMA, trifluralin, pendimethalin, bromoxynil, glyphosate, glufosinate and clomazone. Of those, special mention is to be made of those compositions according to the invention that comprise the compound of formula I and at least one compound selected from the compounds fluometuron, prometryn, metolachlor, α-metolachlor, norflurazon, pyrithiobac-sodium, MSMA and DSMA.

When $R_6$ in formula IV is other than hydrogen, the R-enantiomer of that formula is especially preferred.

Compounds of formula II that are especially suitable for use In the composition according to the invention are those wherein a) A is $A_1$ and E is $E_1$ (common name: asulam) and b) A is $A_2$ and E is $E_2$ (common name: halosulfuron).

Compounds of formula III that are especially suitable for use in the composition according to the invention are listed in Table 1:

TABLE 1

Preferred compounds ot formula III:

(III)

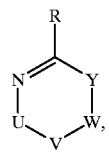

| comp. No. | U—V | W—Y | R | $R_1$ | $R_2$ | $R_3$ | $R_4$ | $R_5$ |
|---|---|---|---|---|---|---|---|---|
| 1.01 | $R_1C$=N | $R_2C$=N | $SCH_3$ | $NHC_2H_5$ | $NHC_3H_7$—(iso) | — | — | — |
| 1.02 | $R_1C$=N | $R_2C$=N | Cl | $NHC_2H_5$ | $NHC_3H_7$—(iso) | — | — | — |
| 1.03 | $CONR_1$ | $CONR_2$ | $N(CH_3)_2$ | cyclohexyl | $CH_3$ | — | — | — |
| 1.04 | $R_1C$=N | $R_2C$=N | $SCH_3$ | $NHC_3H_7$—(iso) | $NHC_3H_7$—(iso) | — | — | — |
| 1.05 | $R_1NCO$ | $R_2C$=$CR_3$ | H | 3-trifluoro-methyl-phenyl | Cl | $NHCH_3$ | — | — |
| 1.06 | $R_1C$=N | $R_2C$=N | Cl | $NHC_2H_5$ | $NHC(CH_3)_2$—CN | — | — | — |
| 1.07 | $R_1C$=$CR_2$ | $CONR_3$ | OH | $CH_3$ | Cl | $C_4H_9$-(tert) | — | — |
| 1.08 | N=$CR_1$ | $R_2NCO$ | $C_4H_9$-(tert) | $SCH_3$ | $NH_2$ | — | — | — |
| 1.09 | $R_1C$=N | $R_2C$=N | $OCH_3$ | $NHC_2H_5$ | $NHC_4H_9$—(tert) | — | — | — |
| 1.10 | $R_1C$=N | $R_2C$=N | $SCH_3$ | $NHC_2H_5$ | $NHC_4H_9$—(tert) | — | — | — |
| 1.11 | —$C(CF_3)$=$C(R_4)$—$C(CH_2$—$C_3H_7$-(iso))=$C(R_4)$— | $CHF_2$ | — | — | — | — | 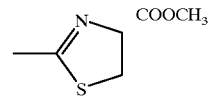 | $COOCH_3$ |
| 1.12 | —$C(CF_3)$=$C(R_4)$—$C(CH_2$—$C_3H_7$-(iso))=$C(R_5)$— | $CHF_2$ | — | — | — | — | $COSCH_3$ | $COSCH_3$ |

The compounds of Table 1 are known by the following names:

| Comp. No. | Common name |
|---|---|
| 1.01 | ametryn |
| 1.02 | atrazine |
| 1.03 | hexazinone |
| 1.04 | prometryn |
| 1.05 | norflurazon |
| 1.06 | cyanazine |
| 1.07 | terbacil |
| 1.08 | metribuzin |
| 1.09 | terbumeton |
| 1.10 | terbutryn |
| 1.11 | thiazopyr |
| 1.12 | dithiopyr |

Compounds of formula IV that are especially suitable for use in the composition according to the invention are listed in Table 2:

TABLE 2

Preferred compounds of formula IV

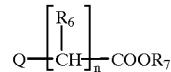

(IV)

| Comp. No. | Q | $R_6$ | $R_7$ | n | common name |
|---|---|---|---|---|---|
| 2.01 | $Q_1$ | — | $-C(CH_3)_2-C(O)O-CH_2CH=CH_2$ | 0 | — |
| 2.02 | $Q_2$ | H | H (and the salts) | 1 | 2,4-D |
| 2.03 | $Q_3$ | — | Na | 0 | pyrithiobac-sodium |
| 2.04 | $Q_4$ | H | H (and the salts) | 1 | glyphosate |
| 2.05 | $Q_5$ | $NH_2$ | H (and the salts) | 1 | glufosinate |
| 2.06 | $Q_6$ | $CH_3$ (R) | $C_2H_5$ | 1 | quizalofop |
| 2.07 | $Q_7$ | $CH_3$ (R) | $C_2H_5$ | 1 | fenoxaprop-P |
| 2.08 | $Q_9$ | $CH_3$ | $C_2H_5$ | 1 | lactofen |
| 2.09 | $Q_8$ | $CH_3$ (R) | $C_4H_9$-(n) | 1 | fluazifop |
| 2.10 | $Q_6$ | $CH_3$ (R) | $C_2H_4ON=C(CH_3)-CH_3$ | 1 | propaquizafop |
| 2.11 | $Q_{10}$ | — | H (and the salts) | 0 | dicamba |

Compounds of formula V that are especially suitable for use in the composition according to the invention are listed in Table 3:

TABLE 3

Preferred compounds of formula V

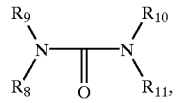

(V)

| Comp. No. | $R_8$ | $R_9$ | $R_{10}$ | $R_{11}$ | common name |
|---|---|---|---|---|---|
| 3.01 | 3,4-dichlorophenyl (structure) | H | $CH_3$ | $CH_3$ | diuron |
| 3.02 | 3-trifluoromethylphenyl | H | $CH_3$ | $CH_3$ | fluometuron |
| 3.03 | 5-tert-butyl-1,3,4-thiadiazol-2-yl (structure) | $CH_3$ | H | $CH_3$ | tebuthiuron |

TABLE 3-continued

Preferred compounds of formula V

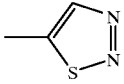

(V)

| Comp. No. | R₈ | R₉ | R₁₀ | R₁₁ | common name |
|---|---|---|---|---|---|
| 3.04 | phenyl | H | H | (thiadiazolyl group) | thidiazuron |

Compounds of formula VI that are especially suitable for use in the composition according to the invention are listed in Table 4:

TABLE 4

Preferred compounds of formula VI:

(VI)

(structure with $R_{14}$, $R_{13}$, $R_{15}$, $R_{16}$, $R_{12}$, X on benzene ring)

| Comp. No. | X | $R_{12}$ | $R_{13}$ | $R_{14}$ | $R_{15}$ | $R_{16}$ | common name |
|---|---|---|---|---|---|---|---|
| 4.01 | N—C₃H₇-(n) | C₃H₇-(n) | 2-NO₂ | 4-CF₃ | 6-NO₂ | H | trifluralin |
| 4.02 | NH | CH(C₂H₅)₂ | 2-NO₂ | 4-CH₃ | 6-NO₂ | 3-CH₃ | pendimethalin |
| 4.03 | | CN | 3-Br | 4-OH | 5-Br | H | bromoxinil |
| 4.04 | N-C₃H₇-(n) | C₃H₇-(n) | 2-NO₂ | 4-CF₃ | 6-NO₂ | 5-NH₂ | prodiamine |

Compounds of formula VII that are especially suitable for use in the composition according to the invention are listed in Table 5:

TABLE 5

Preferred compounds of formula VII:

$$Z-N(R_{17})-R_{18} \quad (VII)$$

| Comp. No. | Z | $R_{17}$ | $R_{18}$ | common name |
|---|---|---|---|---|
| 5.01 | 2-CH₃, 6-C₂H₅-phenyl | —CH(CH₃)—CH₂OCH₃ | —C(O)—CH₂Cl | metolachlor |
| 5.02 | 2-CH₃, 6-C₂H₅-phenyl | —*CH(CH₃)—CH₂OCH₃ (S) | —C(O)—CH₂Cl | α-metolachlor |

TABLE 5-continued

Preferred compounds of formula VII:
Z—N(R$_{17}$)—R$_{18}$    (VII)

| Comp. No. | Z | R$_{17}$ | R$_{18}$ | common name |
|---|---|---|---|---|
| 5.03 | 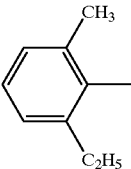 (2,6-substituted phenyl with CH$_3$ and C$_2$H$_5$) | —CH$_2$OC$_2$H$_5$ | —C(O)—CH$_2$Cl | acetochlor |
| 5.04 | 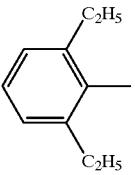 (2,6-diethylphenyl) | —CH$_2$OCH$_3$ | —C(O)—CH$_2$Cl | alachlor |
| 5.05 | 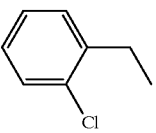 (2-chloro-ethylphenyl) | | —C(O)—C(CH$_3$)$_2$—CH$_2$—O— | clomazone |
| 5.06 | 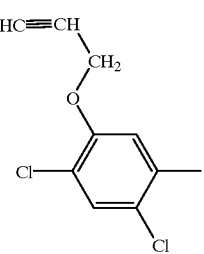 | | 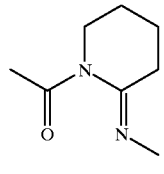 | azafenidine |

Compounds of formula VIII that are especially suitable for use in the composition according to the invention are listed in Table 6:

TABLE 6

Preferred compounds of formula VIII:

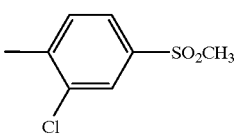

(VIII)

| Comp. No. | X$_a$ | R$_{19}$ | R$_{20}$ | common name |
|---|---|---|---|---|
| 6.01 | NOC$_2$H$_5$ | —CH$_2$—CH(CH$_3$)—<br>SC$_2$H$_5$ | —C$_3$H$_7$-(n) | sethoxydim |
| 6.02 | NOCH$_2$—CH=CHCl<br>(trans) | —CH$_2$—CH(CH$_3$)—<br>SC$_2$H$_5$ | —C$_2$H$_5$ | clethodim |
| 6.03 | O | H | (3-chloro-4-methyl-phenyl with SO$_2$CH$_3$) | sulcotrione |

The monosodium salt of the compound of formula X is known by the name MSMA. The disodium salt of the compound of formula X is known by the name DSMA. The compound of formula IX wherein X is chlorine is known by the name paraquat.

It is extremely surprising that the combination of the active ingredient of formula I with an active ingredient of formula II, III, IV, V, VI, VII, VIII, IX or X surpasses the additive action on the weeds to be controlled that is to be expected in principle, and thus broadens the range of action of both active ingredients especially in two respects: Firstly, the rates of application of the individual compounds I and II, III, IV, V, VI, VII, VIII, IX and X are reduced while a good level of action is maintained. Secondly, the composition according to the invention achieves a high degree of weed control even in cases where the compounds individually, when used at low rates of application, have become no longer useful from an agronomic standpoint. The result of this is a considerable broadening of the weed spectrum and an additional increase in selectivity for crops of useful plants, as is necessary and desirable in case of inadvertent overdosage of the active ingredient. Furthermore, while maintaining outstanding control of weeds in useful plants, the composition according to the invention permits a greater flexibility with regard to subsequent crops. In addition, the onset of action of the compound of formula I can be accelerated in the presence of a mixing partner of formula II, III, IV, V, VI, VII, VIII, IX or X.

The herbicide mixture according to the invention can be used against a large number of agronomically important weeds, such as Stellaria, Agrostis, Digitaria, Avena, Setaria, Sinapis, Lolium, Solanum, Echinochloa, Scirpus, Monochoria, Sagittaria, Bromus, Alopecurus, *Sorghum halepense,* Rottboellia, Cyperus, Abutilon, Sida, Xanthium, Amaranthus, Chenopodium, Ipomoea, Chrysanthemum, Galium, Viola and Veronica. The compositions according to the invention are suitable for all the methods of application usual in agriculture, such as pre-emergence application, post-emergence application and seed dressing. The herbicide mixture according to the invention is suitable especially for weed control in crops of useful plants, such as cereals, rape, sugar beet, sugar cane, plantation crops (cotton), rice, maize and soybeans, more especially in crops of sugar cane and cotton (especially post-emergence application), and also for non-selective weed control.

The compositions according to the invention are especially suitable for controlling the following weeds in crops of sugar cane: *Erigeron canadensis, Convolvulus arvensis, Sorghum halepense, Imperata cylindrica, Cynodon dactylon, Commenlina benghalensis, Cyperus rotundus, Euphorbia heterophylla, Amaranthus retoflexus, Ipomoea hederacea, Brachiaria plantaginea, Digitaria sanguinalis, Eleusine indica, Panicum miliaceum* and *Setaria faberi.* The compositions according to the invention are especially suitable for controlling the following weeds in crops of cotton: *Cyperus rotundus, Sorghum bicolor, Digitaria sanguinalis, Echinochloa crus galli, Eleusine indica, Panicum dichotomiflorum, Setaria faberi, Brachiaria plantaginea,* Abutilon, *Amaranthus retoflexus, Cassia obtusifolia, Chenopodium album, Ipomoea hederacea, Sesbania exaltata* and *Xanthium canadense.* Furthermore, compositions that comprise the compound of formula I and at least one herbicide selected from dithiopyr, prodiamine and simazine are especially suitable for use in lawns. The compound of formula I in combination with flazasulfuron (known from The Pesticide Manual, 9th ed., page 397) and isoxaflutole (known from BRIGHTON CROP PROTECTION CONFERENCE—Weeds—1995, Proceedings Volume 1, pages 35–42) also exhibits a synergistic herbicidal action, especially in sugar cane and lawns. Generally good action is also exhibited by a synergistic mixture consisting of the active ingredient of formula I and azafenidine (known from AGROW, No. 261, Aug. 2, 1996, page 23). Crops are also to be understood as including those which have been made tolerant towards herbicides or classes of herbicides by conventional breeding or genetic engineering techniques, for example maize, soybeans, cotton or sugar cane that is tolerant towards glyphosate, glufosinate, bromoxynil and ALS-inhibitors, such as sulfonylureas (chlorimuron, thifensulfuron), imidazolinone (imazethapyr) or mixtures of those compounds.

The active ingredient combination according to the Invention comprises the active ingredient of formula I and the active ingredient of formula II, III, IV, V, VI, VII, VIII, IX or X in any desired mixing ratio, usually with an excess of the one component over the other. Preferred mixing ratios between the active ingredient of formula I and the mixing partners of formula II, III, IV, V, VI, VII, VIII, IX or X are from 1:1 to 1:350, especially from 1:5 to 1:70. The rate of application can vary within a wide range and depends on the nature of the soil, the type of application (pre- or post-emergence; seed dressing; application to the seed furrow; no tillage application), on the cultivated plant, the weed to be controlled, the prevailing climatic conditions and on other factors determined by the type of application, the time of application and the target crop. In general, the active ingredient mixture according to the invention may be used at a rate of application of from 0.008 to 5 kg/ha, especially from 0.3 to 2 kg/ha active ingredient mixture. The mixtures of the compound of formula I with the compounds of formula II, III, IV, V, VI, VII, VIII, IX or X can be used in unmodified form, i.e. as obtainable from synthesis, but are preferably formulated in customary manner with the adjuvants conventionally employed in formulation technology, such as solvents, solid carriers or surfactants, into e.g. directly sprayable or dilutable solutions, wettable powders, soluble powders, dusts, granules or microcapsules. As with the nature of the compositions, the methods of application, such as spraying, atomising, dusting, wetting, scattering or pouring, are chosen in accordance with the intended objectives and the prevailing circumstances. The formulations, i.e. the compositions, preparations or mixtures comprising the compounds (active ingredients) of formulae I and II, III, IV, V, VI, VII, VIII, IX or X and, where appropriate, one or more solid or liquid formulation adjuvants, are prepared in a manner known per se, e.g. by homogeneously mixing and/or grinding the active ingredients with the formulation adjuvants, e.g. solvents or solid carriers. In addition, surface-active compounds (surfactants) can also be used in the preparation of the formulations.

Suitable solvents are: aromatic hydrocarbons, preferably the fractions containing 8 to 12 carbon atoms, such as xylene mixtures or substituted naphthalenes, phthalates, such as dibutyl or dioctyl phthalate, aliphatic hydrocarbons, such as cyclohexane, or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or N,N-dimethylformamide, and also vegetable oils or epoxidised vegetable oils, such as epoxidised coconut oil or soybean oil, and water. The solid carriers used e.g. for dusts and dispersible powders are normally natural mineral fillers, such as calcite, talcum, kaolin, montmorillonite or attapulgite. In order to improve the physical properties of the formulation it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, such as, especially, dolomite or pulverised plant residues. Depending on the nature of the compound of formula I to be formulated, suitable surface-active compounds are non-ionic, cationic and/or anionic surfactants and mixtures of surfactants having good emulsifying, dispersing and wetting properties. Both so-called water-soluble soaps and water-soluble synthetic surface-active compounds are suitable anionic surfactants. Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of naturally fatty acid mixtures which can be obtained e.g. from coconut oil or tallow oil. Mention may also be made of fatty acid methyltaurine salts. More frequently, however, so-called synthetic surfactants are used, especially fatty alcohol sulfonates, fatty alcohol sulfates, sulfonated benzimidazole derivatives or alkylarylsulfonates. The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or a mixture of fatty alcohol sulfates obtained from natural fatty acids. These compounds also include the salts of sulfated and suffonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 mol of ethylene oxide, or phospholipids. Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Examples of non-ionic surfactants are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol. Fatty acids esters of polyoxyethylenesorbitan, e.g. polyoxyethylene sorbitan trioleate, are also suitable. Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide. The surfactants customarily employed in formulation technology, which can also be used in the compositions according to the invention, are described inter alia in "Mc Cutcheon's Detergents and Emulsifiers Annual" MC Publishing Corp., Ridgewood N.J., 1981, Stache, H., "Tensid-Taschenbuch", Carl Hanser Verlag, Munich/Vienna, 1981 and M. and J. Ash, "Encyclopedia of Surfactants", Vol I–III, Chemical Publishing Co., New York, 1980–81.

The herbicidal formulations usually contain 0.1 to 99% by weight, especially 0.1 to 95% by weight, of an active ingredient mixture of the compound of formula I with the compounds of formula II, III, IV, V, VI, VII, VIII, IX or X, 1 to 99.9% by weight of a solid or liquid adjuvant, and 0 to 25% by weight, especially 0.1 to 25% by weight, of a surfactant. Whereas commercial products are preferably formulated as concentrates, the end user will normally employ dilute formulations. The compositions may also comprise further ingredients, such as stabilisers, for example vegetable oils or epoxidised vegetable oils (epoxidised coconut oil, rape oil or soybean oil), antifoams, for example silicone oil, preservatives, viscosity regulators, binders, tackifiers, as well as fertilisers or other active ingredients.

Preferred formulations are composed in particular of the following constituents (throughout, percentages are by weight):

Dusts:
active ingredient mixture: 0.1 to 10%, preferably 0.1 to 5%
solid carrier: 99.9 to 90%, preferably 99.9 to 99%

Suspension concentrates:
active ingredient mixture: 5 to 75%, preferably 10 to 50%
water: 94 to 24%, preferably 88 to 30%
surfactant 1 to 40%, preferably 2 to 30%

Wettable powders:
active ingredient mixture: 0.5 to 90%, preferably 1 to 80%
surfactant: 0.5 to 20%, preferably 1 to 15%
solid carrier: 5 to 95%, preferably 15 to 90%

Granules:
active ingredient mixture: 0.1 to 30%, preferably 0.1 to 15%
solid carrier: 99.5 to 70%, preferably 97 to 85%

The following Examples illustrate the invention in more detail without limiting it.

FORMULATION EXAMPLES FOR MIXTURES OF COMPOUNDS OF FORMULAE I AND II, III, IV, V, VI, VI, VIII, IX OR X (THROUGHOUT, PERCENTAGES ARE BY WEIGHT):

| F1. Solutions | a) | b) | c) | d) |
|---|---|---|---|---|
| compound I + according to Tables 1–6 | 5% | 10% | 50% | 90% |
| 1-methoxy-3-(3-methoxy-propoxy)-propane | — | 20% | 20% | — |
| polyethylene glycol mol. wt. 400 | 20% | 10% | — | — |
| N-methyl-2-pyrrolidone | — | — | 30% | 10% |
| arom. hydrocarbon mixture $C_9$–$C_{12}$ | 75% | 60% | — | — |

The solutions are suitable for use in the form of micro-drops.

| F2. Wettable powders | a) | b) | c) | d) |
|---|---|---|---|---|
| compound I + according to Tables 1–6 | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7–8 mol of ethylene oxide) | — | 1% | 2% | — |
| highly dispersed silicic acid | 1% | 3% | 5% | 10% |
| kaolin | 88% | 62% | 35% | — |

The active ingredients are thoroughly mixed with the adjuvants and the mixture is thoroughly ground in a suitable mill, affording wettable powders which can be diluted with water to give suspensions of any desired concentration.

| F3. Coated granules | a) | b) | c) |
|---|---|---|---|
| compound I + according to Tables 1–6 | 0.1% | 5% | 15% |
| highly dispersed silicic acid | 0.9% | 2% | 2% |
| inorg. carrier (Æ 0.1–1 mm) e.g. CaCO$_3$ or SiO$_2$ | 99.0% | 93% | 83% |

The active ingredients are dissolved in methylene chloride, the solution is sprayed onto the carrier and the solvent is subsequently evaporated off in vacuo.

| F4. Coated granules | a) | b) | c) |
|---|---|---|---|
| compound I + according to Tables 1–6 | 0.1% | 5% | 15% |
| polyethylene glycol mol. wt. 200 | 1.0% | 2% | 3% |
| highly dispersed silicic acid | 0.9% | 1% | 2% |
| inorg. carrier (Æ 0.1–1 mm) e.g. CaCO$_3$ or SiO$_2$ | 98.0% | 92% | 80% |

The finely ground active ingredients are uniformly applied, in a mixer, to the carrier moistened with polyethylene glycol. Non-dusty coated granules are obtained in this manner.

| F5. Extruder granules | a) | b) | c) | d) |
|---|---|---|---|---|
| compound I + according to Tables 1–6 | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredients are mixed and ground with the adjuvants, and the mixture is moistened with water. The mixture is extruded and then dried in a stream of air.

| F6. Dusts | a) | b) | c) |
|---|---|---|---|
| compound I + according to Tables 1–6 | 0.1% | 1% | 5% |
| talcum | 39.9% | 49% | 35% |
| kaolin | 60.0% | 50% | 60% |

Ready-for-use dusts are obtained by mixing the active ingredients with the carriers and grinding the mixture in a suitable mill.

| F7. Suspension concentrates | a) | b) | c) | d) |
|---|---|---|---|---|
| compound I + according to Tables 1–6 | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

It is often more practical to formulate the compound of formula I and the mixing partners of formula II, III, IV, V, VI, VII, VIII, IX or X individually and subsequently combine them in the desired mixing ratio as a tank mix in water shortly before application in an applicator.

BIOLOGICAL EXAMPLES

A synergistic effect exists whenever the action of the active ingredient combination I and II, III, IV, V, VI, VII, VIII, IX or X is greater than the sum of the actions of the active ingredients applied individually. The herbicidal action to be expected, We, for a given combination of two herbicides can be calculated as follows (see COLBY, S. R. "Calculating synergistic and antagonistic response of herbicide combinations". Weeds 15, pages 20–22; 1967):

$$We = X + [Y \cdot (100-X)/100]$$

wherein:
X=% herbicidal action in the case of treatment with the compound of formula I using an application rate of p kg per hectare, in comparison with untreated control (=0%).
Y=% herbicidal action in the case of treatment with a compound of formula II, III, IV, V, VI, VII, VIII, IX or X using an application rate of q kg per hectare, in comparison with untreated control.
We=expected herbicidal action (% herbicidal action in comparison with untreated control) after treatment with the compounds of formula I and II, III, IV, V, VI, VII, VIII, IX or X at a rate of application of p+q kg of active ingredient per hectare.

If the action actually observed is greater than the expected value We, then synergy exists. The synergistic effect of the combinations of the active ingredient of formula I with the active ingredients of formula II, III, IV, V, VI, VII, VIII, IX or X is demonstrated in the following Example.

EXAMPLE B1

Pre-emergence Herbicidal Action

Monocotyledonous and dicotyledonous weeds and cultivated plants are sown in standard soil in plastics pots. Immediately after sowing, the test compounds are applied as an aqueous suspension (500 l of water/ha). The rates of application depend on the optimum concentrations determined under field conditions and greenhouse conditions. Evaluation of the tests is made after 15 and 27 days (DAA=day after application) in % action. 100% denotes that the plants have died, 0% denotes no phytotoxic action. The combinations of the active ingredient of formula I with the active ingredients of formula II, III, IV, V, VI, VII, VIII, IX or X exhibit a synergistic action in this test. Examples of the pre-emergence synergistic action of the compositions according to the invention are given in the following Tables:

TABLE B1

Pre-emergence herbicidal action of the composition according to the invention comprising the compound of formula I and prometryn on DAA 15

| rate of application test plant | comp. of formula I 3.75 g/ha | prometryn 250 g/ha | 3.75 g/ha + 250 g/ha prometryn | expected value according to Colby |
|---|---|---|---|---|
| Sesbania | 35 | 10 | 50 | 42 |
| Xanthium | 85 | 0 | 90 | 85 |

TABLE B2

Pre-emergence herbicidal action of the composition according to the invention comprising the compound of formula I and prometryn on DAA 27

| rate of application test plant | comp. of formula I 3.75 g/ha | prometryn 250 g/ha | 3.75 g/ha + 250 g/ha prometryn | expected value according to Colby |
|---|---|---|---|---|
| Digitaria | 25 | 10 | 80 | 33 |
| Sesbania | 25 | 0 | 35 | 25 |
| Brachiaria | 25 | 10 | 60 | 33 |
| Abutilon | 50 | 0 | 85 | 50 |

TABLE B3

Pre-emergence herbicidal action of the composition according to the invention comprising the compound of formula I and norflurazon on DAA 27:

| rate of application test plant | comp. of formula I 3.75 g/ha | norflurazon 500 g/ha | norflurazon 250 g/ha | 3.75 g/ha 1 + 500 g/ha norflurazon | expected value according to Colby | 3.75 g/ha 1 + 250 g/ha norflurazon | expected value according to Colby |
|---|---|---|---|---|---|---|---|
| cotton | 10 | 0 | 0 | 0 | 10 | 0 | 10 |
| Abutilon | 50 | 60 | 60 | 96 | 80 | 96 | 80 |
| Sesbania | 25 | 30 | 10 | 50 | 48 | 30 | 32 |
| Xanthium | 96 | 35 | 10 | 98 | 97 | 98 | 96 |

In addition to the synergistic herbicidal action of the composition according to the invention on the weeds, surprisingly an advantageous antagonistic action on the cultivated plant cotton was found, i.e. whereas the compound of formula I when applied at-a rate of 3.75 g/ha damages cotton by 10%, when 500 or 250 g/ha of norflurazon are added to the compound of formula I the cotton is protected to a very large extent (0% damage) while the herbicidal action on the weeds is increased.

TABLE B4

Pre-emergence herbicidal action of the composition according to the invention comprising the compound of formula I and pendimethalin on DAA 15

| rate of application/herbicide | herbicidal action on Xanthium | expected value according to Colby |
|---|---|---|
| 7.5 g/ha compound of formula I | 90 | — |
| 3.75 g/ha compound of formula I | 85 | — |
| 1000 g/ha pendimethalin | 0 | — |
| 500 g/ha pendimethalin | 0 | — |
| 250 g/ha pendimethalin | 0 | — |
| 7.5 g/ha I + 1000 g/ha pendimethalin | 97 | 90 |
| 7.5 g/ha I + 500 g/ha pendimethalin | 97 | 90 |
| 7.5 g/ha I + 250 g/ha pendimethalin | 95 | 90 |
| 3.75 g/ha I + 1000 g/ha pendimethalin | 90 | 85 |
| 3.75 g/ha I + 500 g/ha pendimethalin | 95 | 85 |
| 3.75 g/ha I + 250 g/ha pendimethalin | 95 | 85 |

TABLE B5

Pre-emergence herbicidal action of the composition according to the invention comprising the compound of formula I and clomazone on DAA 15

| rate of application/herbicide | herbicidal action on Xanthium | expected value according to Colby |
|---|---|---|
| 3.75 g/ha compound of formula I | 85 | — |
| 500 g/ha clomazone | 60 | — |
| 250 g/ha clomazone | 25 | — |
| 125 g/ha clomazone | 10 | — |
| 3.75 g/ha I + 500 g/ha clomazone | 95 | 94 |
| 3.75 g/ha I + 250 g/ha clomazone | 95 | 89 |
| 3.75 g/ha I + 125 g/ha clomazone | 95 | 87 |

EXAMPLE B2

Post-emergence Herbicidal Action

The test plants are raised in plastics pots under greenhouse conditions as far as the 2- to 3-leaf stage. A standard soil is used as the cultivation substrate. At the 2- to 3-leaf stage, the herbicides are applied individually and as mixtures to the test plants. The test compounds are applied in the form of an aqueous suspension in 500 l of water/ha. The rates of application depend on the optimum concentrations determined under field conditions and greenhouse conditions. Evaluation of the tests is made after 11 and 22 days (DAA=day after application) in % action. 100% denotes that the plants have died, 0% denotes no phytotoxic action. The combinations of the active ingredient of formula I with the active ingredients of formula II, III, IV, V, VI, VII, VIII, IX or X exhibit a synergistic action in this test. Examples of the post-emergence synergistic action of the compositions according to the invention are given in the following Tables.

TABLE B6

Pre-emergence herbicidal action of the composition according to the invention comprising the compound of formula I and fluometuron on DAA 11

| rate of application/herbicide | herbicidal action on Cyperus | expected value according to Colby |
|---|---|---|
| 3.75 g/ha compound of formula I | 50 | — |
| 1000 g/ha fluometuron | 20 | — |
| 500 g/ha fluometuron | 25 | — |
| 250 g/ha fluometuron | 0 | — |
| 3.75 g/ha I + 1000 g/ha fluometuron | 70 | 60 |
| 3.75 g/ha I + 500 g/ha fluometuron | 70 | 63 |
| 3.75 g/ha I + 250 g/ha fluometuron | 60 | 50 |

TABLE B7

Pre-emergence herbicidal action of the composition according to the invention comprising the compound of formula I and prometryn on DAA 22

| rate of application/herbicide | herbicidal action on Solanum nigrum | expected value according to Colby |
|---|---|---|
| 7.5 g/ha compound of formula I | 15 | — |
| 3.75 g/ha compound of formula I | 0 | — |
| 1.88 g/ha compound of formula I | 0 | — |
| 1000 g/ha prometryn | 20 | — |
| 500 g/ha prometryn | 0 | — |
| 250 g/ha prometryn | 0 | — |
| 7.5 g/ha I + 1000 g/ha prometryn | 35 | 32 |
| 7.5 g/ha I + 500 g/ha prometryn | 25 | 15 |
| 7.5 g/ha I + 250 g/ha prometryn | 25 | 15 |
| 3.75 g/ha I + 1000 g/ha prometryn | 50 | 20 |
| 3.75 g/ha I + 500 g/ha prometryn | 45 | 0 |
| 3.75 g/ha I + 250 g/ha prometryn | 10 | 0 |
| 1.88 g/ha I + 1000 g/ha prometryn | 30 | 20 |
| 1.88 g/ha I + 500 g/ha prometryn | 25 | 0 |
| 1.88 g/ha I + 250 g/ha prometryn | 25 | 0 |

TABLE B8

Pre-emergence herbicidal action of the composition according to the invention comprising the compound of formula I and metolachlor on DAA 22

| rate of application/herbicide | herbicidal action on Sorghum hal. | expected value according to Colby |
|---|---|---|
| 1.88 g/ha compound of formula I | 75 | — |
| 1500 g/ha metolachlor | 0 | — |
| 750 g/ha metolachlor | 0 | — |
| 375 g/ha metolachlor | 0 | — |
| 1.88 g/ha I + 1500 g/ha metolachlor | 90 | 75 |
| 1.88 g/ha I + 750 g/ha metolachlor | 95 | 75 |
| 1.88 g/ha I + 375 g/ha metolachlor | 92 | 75 |

TABLE B9

Pre-emergence herbicidal action of the composition according to the invention comprising the compound of formula I and α-metolachlor on Abutilon on DAA 22

| rate of application/herbicide | herbicidal action on Abutilon | expected value according to Colby |
|---|---|---|
| 1.88 g/ha compound of formula I | 55 | — |
| 500 g/ha α-metolachlor | 0 | — |
| 250 g/ha α-metolachlor | 0 | — |
| 1.88 g/ha I + 500 g/ha α-metolachlor | 65 | 66 |
| 1.88 g/ha I + 250 g/ha α-metolachlor | 95 | 66 |

TABLE B10

Post-emergence herbicidal action of the composition according to the invention comprising the compound of formula I and α-metolachlor on Cassia sp. on DAA 11

| rate of application/herbicide | herbicidal action on Cassia sp. | expected value according to Colby |
|---|---|---|
| 1.88 g/ha compound of formula 1 | 70 | — |
| 1000 g/ha α-metolachlor | 0 | — |
| 500 g/ha α-metolachlor | 0 | — |
| 250 g/ha α-metolachlor | 0 | — |
| 1.88 g/ha I + 1000 g/ha α-metolachlor | 90 | 70 |
| 1.88 g/ha I + 500 g/ha α-metolachlor | 80 | 70 |
| 1.88 g/ha I + 250 g/ha α-metolachlor | 90 | 70 |

TABLE B11

Post-emergence herbicidal action of the composition according to the invention comprising the compound of formula I and α-metolachlor on Ipomoea on DAA 11

| rate of application/herbicide | herbicidal action on Ipomoea | expected value according to Colby |
|---|---|---|
| 1.88 g/ha compound of formula I | 80 | — |
| 1000 g/ha α-metolachlor | 0 | — |
| 500 g/ha α-metolachlor | 0 | — |
| 250 g/ha α-metolachlor | 0 | — |
| 1.88 g/ha I + 1000 g/ha α-metolachlor | 90 | 80 |
| 1.88 g/ha I + 500 g/ha α-metolachlor | 90 | 80 |
| 1.88 g/ha I + 250 g/ha α-metolachlor | 85 | 80 |

TABLE B12

Post-emergence herbicidal action of the composition according to the invention comprising the compound of formula I and α-metolachlor on Sesbania on DAA 11

| rate of application/herbicide | herbicidal action on Sesbania | expected value according to Colby |
|---|---|---|
| 1.88 g/ha compound of formula I | 70 | — |
| 1000 g/ha α-metolachlor | 0 | — |
| 500 g/ha α-metolachlor | 0 | — |
| 250 g/ha α-metolachlor | 0 | — |
| 1.88 g/ha I + 1000 g/ha α-metolachlor | 85 | 70 |
| 1.88 g/ha I + 500 g/ha α-metolachlor | 80 | 70 |
| 1.88 g/ha I + 250 g/ha α-metolachlor | 85 | 70 |

TABLE B13

Post-emergence herbicidal action of the composition according to the invention comprising the compound of formula I and α-metolachlor on Xanthium on DAA 11

| rate of application/herbicide | herbicidal action on Xanthium | expected value according to Colby |
|---|---|---|
| 1.88 g/ha compound of formula I | 85 | — |
| 1000 g/ha α-metolachlor | 0 | — |
| 500 g/ha α-metolachlor | 0 | — |
| 250 g/ha α-metolachlor | 0 | — |
| 1.88 g/ha I + 1000 g/ha α-metolachlor | 95 | 85 |
| 1.88 g/ha I + 500 g/ha α-metolachlor | 95 | 85 |
| 1.88 g/ha I + 250 g/ha α-metolachlor | 95 | 85 |

TABLE B14

Post-emergence herbicidal action of the composition according to the invention comprising the compound of formula I and pyrithiobac on DAA 11

| rate of application/herbicide | herbicidal action on Cassia sp. | expected value according to Colby |
|---|---|---|
| 1.88 g/ha compound of formula I | 70 | — |
| 100 g/ha pyrithiobac | 70 | — |
| 50 g/ha pyrithiobac | 80 | — |
| 25 g/ha pyrithiobac | 50 | — |
| 1.88 g/ha I + 100 g/ha pyrithiobac | 95 | 91 |
| 1.88 g/ha I + 50 g/ha pyrithiobac | 95 | 94 |
| 1.88 g/ha I + 25 g/ha pyrithiobac | 95 | 85 |

TABLE B15

Post-emergence herbicidal action of the composition according to the invention comprising the compound of formula I and MSMA on Cassia sp. DAA 11

| rate of application/herbicide | herbicidal action on Cassia sp. | expected value according to Colby |
|---|---|---|
| 1.88 g/ha compound of formula I | 70 | — |
| 2000 g/ha MSMA | 50 | — |
| 1000 g/ha MSMA | 20 | — |
| 500 g/ha MSMA | 0 | — |
| 1.88 g/ha I + 2000 g/ha MSMA | 85 | 85 |
| 1.88 g/ha I + 1000 g/ha MSMA | 95 | 76 |
| 1.88 g/ha I + 500 g/ha MSMA | 95 | 70 |

TABLE B16

Post-emergence herbicidal action of the composition according to the invention comprising the compound of formula I and MSMA on Sesbania on DAA 11

| rate of application/herbicide | herbicidal action on Sesbania | expected value according to Colby |
|---|---|---|
| 1.88 g/ha compound of formula I | 70 | — |
| 2000 g/ha MSMA | 20 | — |
| 1000 g/ha MSMA | 0 | — |
| 500 g/ha MSMA | 0 | — |
| 1.88 g/ha I + 2000 g/ha MSMA | 90 | 76 |
| 1.88 g/ha I + 1000 g/ha MSMA | 90 | 70 |
| 1.88 g/ha I + 500 g/ha MSMA | 90 | 70 |

TABLE B17

Post-emergence herbicidal action of the composition according to the invention comprising the compound of formula I and bromoxynil on Solanum on DAA 11

| rate of application/herbicide | herbicidal action on Solanum | expected value according to Colby |
|---|---|---|
| 7.5 g/ha compound of formula I | 20 | — |
| 1000 g/ha bromoxynil | 40 | — |
| 500 g/ha bromoxynil | 35 | — |
| 7.5 g/ha I + 1000 g/ha bromoxynil | 80 | 52 |
| 7.5 g/ha I + 500 g/ha bromoxynil | 50 | 48 |

TABLE B18

Post-emergence herbicidal action of the composition according to the invention comprising the compound of formula I and glyphosate on DAA 11

| rate of application test plant | comp. of formula I 1.88 g/ha | glyphosate 187 g/ha | 1.88 g/ha I + 187 g/ha glyphosate | expected value according to Colby |
|---|---|---|---|---|
| Abutilon | 75 | 30 | 90 | 83 |
| Cassia | 70 | 40 | 90 | 82 |
| Digitaria | 25 | 85 | 95 | 89 |
| Ipomoea | 80 | 30 | 90 | 86 |
| Sesbania | 70 | 60 | 90 | 88 |
| Sorghum | 70 | 40 | 85 | 82 |

TABLE B19

Post-emergence herbicidal action of the composition according to the invention comprising the compound of formula I and glufosinate on DAA 22

| rate of application test plant | comp. of formula I 1.88 g/ha | glufosinate 250 g/ha | 1.88 g/ha I + 250 g/ha glufosinate | expected value according to Colby |
|---|---|---|---|---|
| Abutilon | 55 | 55 | 90 | 80 |
| Cyperus | 70 | 35 | 85 | 81 |
| Digitaria | 15 | 75 | 97 | 79 |
| Sorghum | 75 | 85 | 98 | 96 |

What is claimed is:

1. A herbicidal synergistic composition which comprises, in addition to conventional inert formulation adjuvants, the compound of formula I (I)

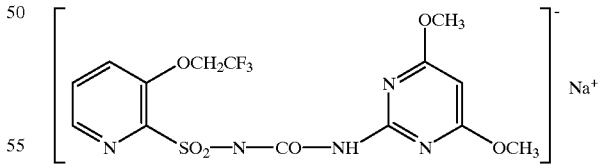

in admixture with a second component comprising at least one compound selected from the group consisting of ametryn, atrazine, hexazinone, asulam, diuron, 2,4-D, halosulfuron and a compound of formula IV (IV)

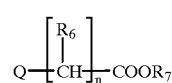

wherein
n is 0,
$R_7$ is $-C(CH_3)_2-CO_2CH_2CH=CH_2$, and
Q is the group

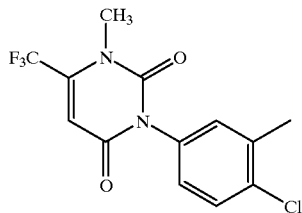

(Q₁)

and salts thereof.

2. A herbicidal composition according to claim 1, wherein the component of formula I is present in a weight ratio of from 1:100 to 1000:1 in relation to the second component.

3. A method of controlling undesired plant growth in crops of useful plants, which comprises allowing a herbicidally effective amount of a composition according to claim 1 to act on the cultivated plant or the locus thereof.

4. A method according to claim 3, wherein the cultivated plant is cotton or sugar cane.

5. A method according to claim 4, wherein the crops of useful plants are treated with said composition at rates of application corresponding to from 0.008 to 5 kg/ha total amount of active ingredients per hectare.

* * * * *